United States Patent
Nallakrishnan

(12) 
(10) Patent No.: US 9,247,954 B2
(45) Date of Patent: Feb. 2, 2016

(54) SAFETY KNIFE WITH RETRACTABLE AND EXTENDABLE BLADE AND GUARD

(75) Inventor: Ravi Nallakrishnan, Westmont, IL (US)

(73) Assignee: Ravi Nallakrishnan Revocable Trust, Willowbrook, IL (US)

( * ) Notice: Subject to any disclaimer, the term of this patent is extended or adjusted under 35 U.S.C. 154(b) by 118 days.

(21) Appl. No.: 13/092,020

(22) Filed: Apr. 21, 2011

(65) Prior Publication Data

US 2015/0073449 A1    Mar. 12, 2015

Related U.S. Application Data

(60) Provisional application No. 61/326,225, filed on Apr. 21, 2010.

(51) Int. Cl.
| | | |
|---|---|---|
| *A61B 17/3211* | (2006.01) | |
| *A61F 9/013* | (2006.01) | |
| *A61B 19/00* | (2006.01) | |

(52) U.S. Cl.
CPC ........... *A61B 17/3211* (2013.01); *A61F 9/0133* (2013.01); *A61B 2017/32113* (2013.01); *A61B 2019/4805* (2013.01)

(58) Field of Classification Search
CPC .................. A61B 17/3211; A61B 2017/32113; A61B 2019/4805
See application file for complete search history.

(56) References Cited

U.S. PATENT DOCUMENTS

| | | | | |
|---|---|---|---|---|
| 5,250,063 | A | * | 10/1993 | Abidin et al. .................. 606/167 |
| 5,309,641 | A | * | 5/1994 | Wonderley et al. ............. 30/339 |
| 5,569,282 | A | * | 10/1996 | Werner ......................... 606/167 |
| 5,827,309 | A | * | 10/1998 | Jolly et al. .................... 606/167 |
| 6,176,017 | B1 | * | 1/2001 | Sato et al. ..................... 30/277.4 |
| 6,569,175 | B1 | * | 5/2003 | Robinson ...................... 606/166 |
| 7,101,382 | B2 | * | 9/2006 | George et al. ................. 606/167 |
| 8,464,430 | B2 | * | 6/2013 | Cote ............................... 30/162 |
| 8,814,893 | B2 | * | 8/2014 | Cote et al. ..................... 606/167 |
| 2005/0028386 | A1 | * | 2/2005 | Hughes ......................... 30/298.4 |
| 2009/0192538 | A1 | * | 7/2009 | Sandel et al. ................. 606/167 |
| 2009/0204135 | A1 | * | 8/2009 | Cote ............................. 606/167 |
| 2010/0137894 | A1 | * | 6/2010 | Ueno et al. .................... 606/167 |
| 2011/0092994 | A1 | * | 4/2011 | Nallakrishnan ............... 606/167 |
| 2012/0215241 | A1 | * | 8/2012 | Trees et al. .................... 606/167 |
| 2013/0158574 | A1 | * | 6/2013 | Yi et al. ......................... 606/167 |

* cited by examiner

*Primary Examiner* — Hwei C Payer
(74) *Attorney, Agent, or Firm* — Wood, Phillips, Katz, Clark & Mortimer

(57) ABSTRACT

A safety surgical knife has a blade guard and a knife blade holder. The knife blade is covered when the guard is extended to protect it. When the blade is extended to its full operating position the guard is simultaneously retracted. When the blade is retracted the guard is simultaneously extended to return to its protective position. A shaped knife handle acts as an orientation guide and an anti-roll prop keeps the knife from rolling over when placed on a flat surface.

8 Claims, 10 Drawing Sheets

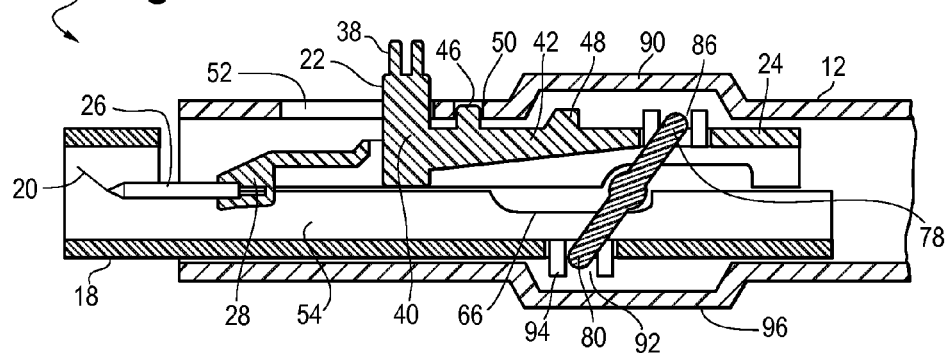
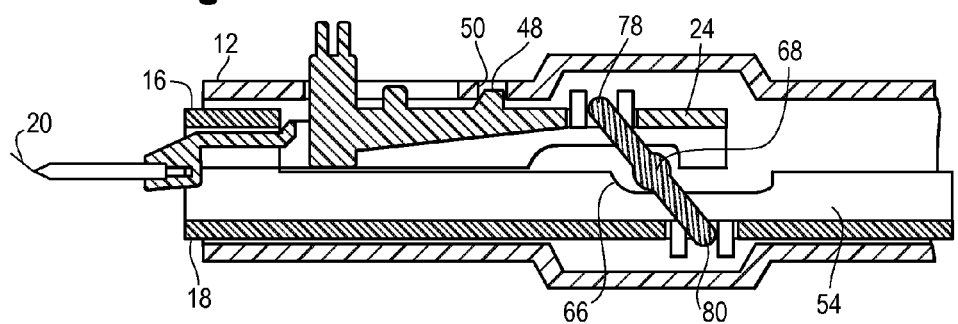
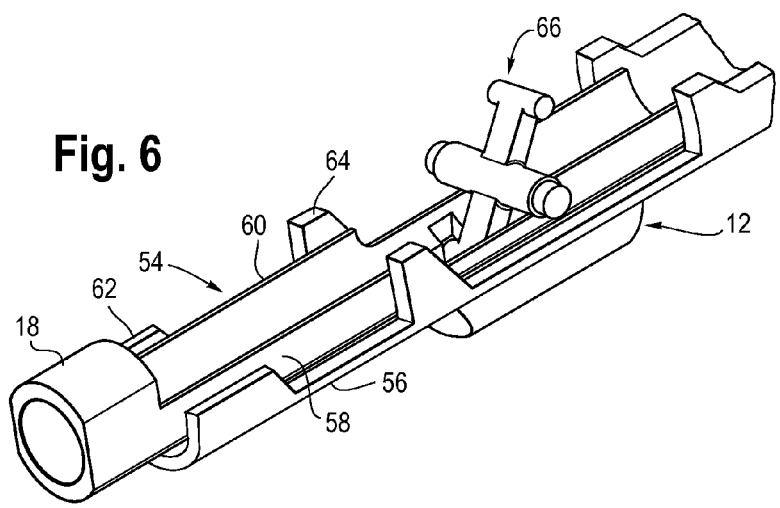

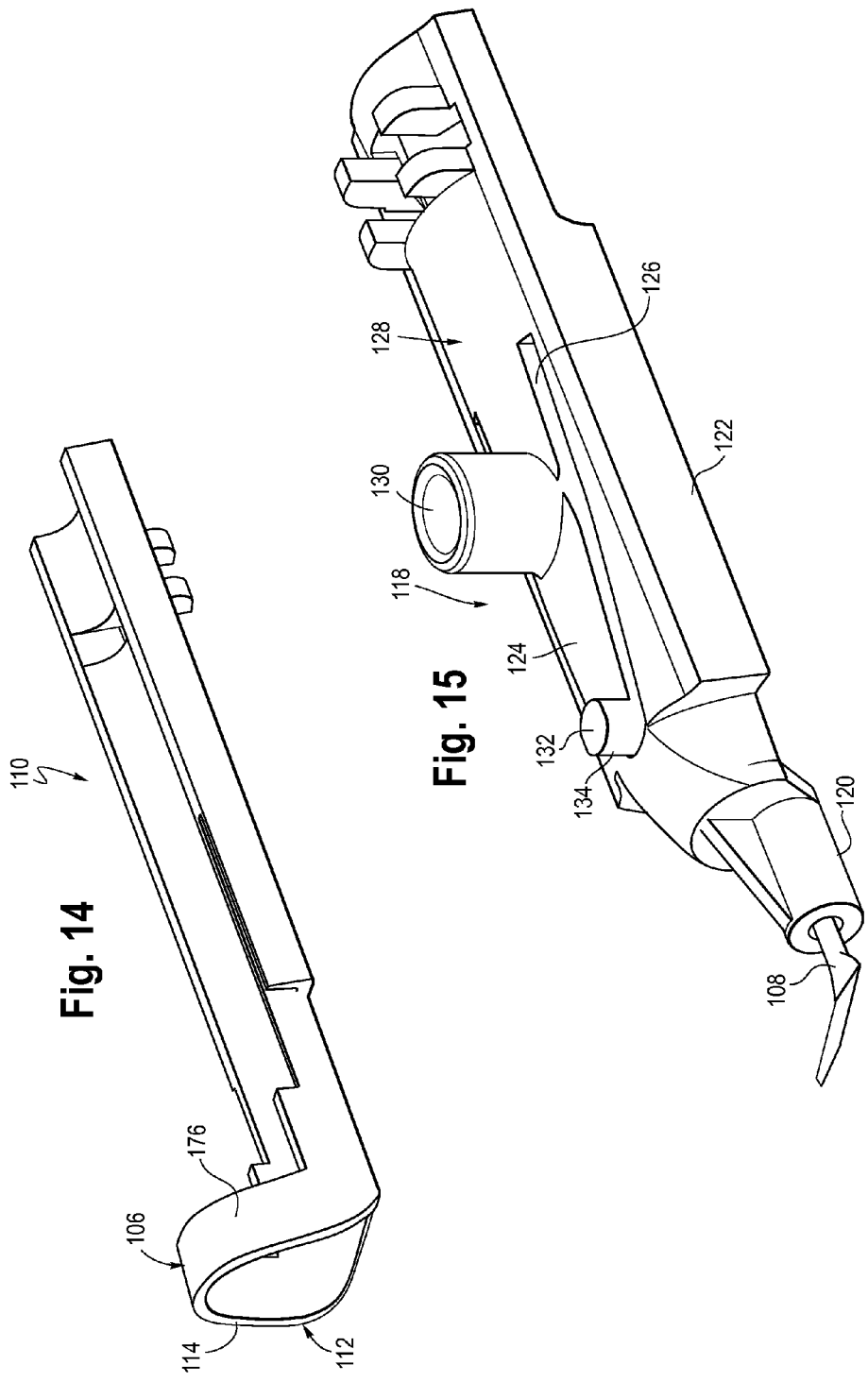

SAFETY KNIFE WITH RETRACTABLE AND EXTENDABLE BLADE AND GUARD

The present invention is a continuation-in-part of, and claims priority from, U.S. Provisional Patent Application Ser. No. 61/326,225, filed 21 Apr. 2010 and entitled "Safety Knife With Retractable Blade and Guard", the entirety of which is hereby incorporated herein by reference.

The present invention relates to knives used for surgery and, in particular, a safety surgical knife having a blade guard and a knife blade holder. The knife blade is covered when the guard is extended to protect it. When the blade is extended to its full operating position the guard is simultaneously retracted. When the blade is retracted the guard is simultaneously extended to return to its protective position.

BACKGROUND OF THE INVENTION

Knives and scalpels used in ophthalmic surgery have small, extremely sharp blades. During eye surgery it is desirable to make the incisions as small as possible to allow for faster healing and to obviate the need for stitching the incision closed after surgery has been completed.

Surgical instruments are typically arranged by a surgical assistant and passed to the surgeon as needed. When the surgeon is finished using a particular instrument, it is customary for the surgeon to pass the instrument back to the assistant who then retains it for further use or, if use is completed, disposes of the instrument.

Operating in as confined a surgical field as the eye requires dexterity, concentration and, often, the use of microscopes or other magnifying devices to allow the surgeon to more clearly visualize the eye tissue. A constant concern during surgical procedures is the accidental cutting of either the surgeon or the assistant by an exposed cutting blade. Accidental cutting may cause serious injury and will also require that the person cut be regloved before surgery can continue.

It is known to provide scalpels and knives with blade covers or blade guards to protect the blade itself prior to surgery and to protect the blade users during surgery. Examples of such blade guards are found in the prior art.

U.S. Pat. No. 7,022,128 (Morawsky) teaches and describes a surgical knife safety handle having a blade guard that can be extended from and retracted into the handle.

U.S. Pat. No. D496,730 (Morawsky et al) teaches and describes an ornamental design for surgical knife safety handle corresponding to the knife described and claimed in the '128 patent.

U.S. Pat. No. 6,626,925 (Newman et al) teaches and describes a shielded surgical scalpel having an extendable and retractable blade guard.

A common drawback to the designs shown in the aforementioned references is the necessity for the surgeon to maintain either an uncomfortable hand position during retraction and extension of the guard, or the need for the surgeon to grip the knife in a first position to operate the blade guard, then change grips, or "walk the handle" to use the knife to make incisions. Repositioning the surgeon's hand after retracting the guard often means that the surgeon's attention and concentration is diverted from the operating field to the knife itself.

It is good surgical procedure to have the guard in place when the knife is passed back and forth between the assistant and the surgeon. Prior knife designs tend to require the surgeon's hand to be repositioned to extend the guard after the surgeon's use of the knife is completed before passing the knife back to the surgical assistant.

Commonly, the assistant already has the next instrument to be used in one hand ready to pass to the surgeon, while receiving the used instrument in the other hand. It would be awkward and dangerous for the surgical assistant to take a knife with the guard retracted and use a single hand to extend the guard before disposing of the knife.

Prior art safety handle designs thus make the extension and retraction of the guard awkward and uncomfortable by requiring repositioning of the user's hand to extend and retract the guard.

The present invention provides a safety knife with a knife blade guard that can be extended to protect the blade and retracted to expose the blade with limited repositioning of the user's hand. When the guard is extended, the blade is simultaneously retracted so that no portion of the blade extends past the guard. When the guard is retracted, the blade is extended to its full operative position.

The present invention also provides a safety knife designed to allow the movement of both the guard and blade with a single actuator.

The present design also provides a guard which allows the blade to be fully observed when the guard is in the extended position and the blade is in the retracted position.

The present invention also provides a safety knife which is economical to manufacture and simple to use.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further aspects of the present invention will best be appreciated upon considering the accompanying drawing wherein:

FIG. 4 is a partial lateral sectional view of the knife of FIG. 1 with the guard extended and the blade retracted;

FIG. 5 is a partial lateral sectional view of the knife of FIG. 1 showing the guard retracted and the blade extended;

FIG. 6 is a perspective view of the guard carriage, lower housing and pivot pin disassembled from the knife of FIG. 1;

FIG. 14 is a perspective view of the guard of the device shown in FIG. 13;

FIG. 15 is a perspective view of the blade carriage of the device shown in FIG. 13;

DETAILED DESCRIPTION OF THE INVENTION

Figure 1:
FIG. 1 is a perspective view of a surgical safety knife embodying certain principles of the present invention, shown with the blade guard extended and the blade partially retracted.

Referring now to FIG. 1, the numeral 10 identifies a surgical safety knife having a handle 12 with a proximal end 14 and a distal end 16. A blade guard 18 extends from distal end 16 of handle 12 and is preferably sized and shaped to surround and protect a surgical blade 20 which also extends from distal end 16.

Figure 2:
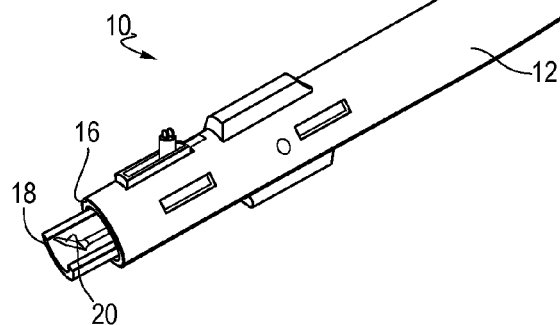
FIG. 2 is an enlarged view of the tip of the knife shown in FIG. 1 with the guard extended.

Referring now to FIG. 2, an enlarged detail is shown of distal end 16. Preferably guard 18 is formed from a transparent plastic to allow blade 20 to be viewed when guard 18 is extended. This allows the surgeon to identify the type and orientation of blade 20. An actuator 22 is shown slidably mounted to handle 12 in a manner to be described hereinbelow. In FIG. 2, actuator 22 is shown in its rearmost or retracted position and it is in this position that guard 18 is extended and blade 20 is retracted.

Figure 3:
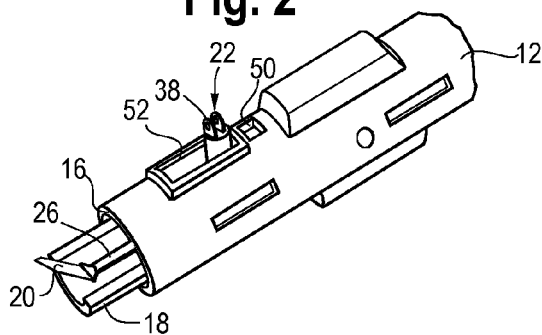
FIG. 3 is a view of FIG. 2 with the guard retracted and the blade fully extended.

Referring now to FIG. 3, actuator 22 is shown in its forwardmost or extended position. In this position, guard 18 is retracted into handle 12 and blade 20 is fully extended from handle 12 at distal end 16 to its operating position.

Referring now to FIG. 4, a partial lateral sectional view of knife 10 is shown with guard 18 in its extended position. As seen in FIG. 4, handle 12 is hollow and slidably accommodates a guard carriage and needle carriage to be described hereinbelow.

Figure 8:
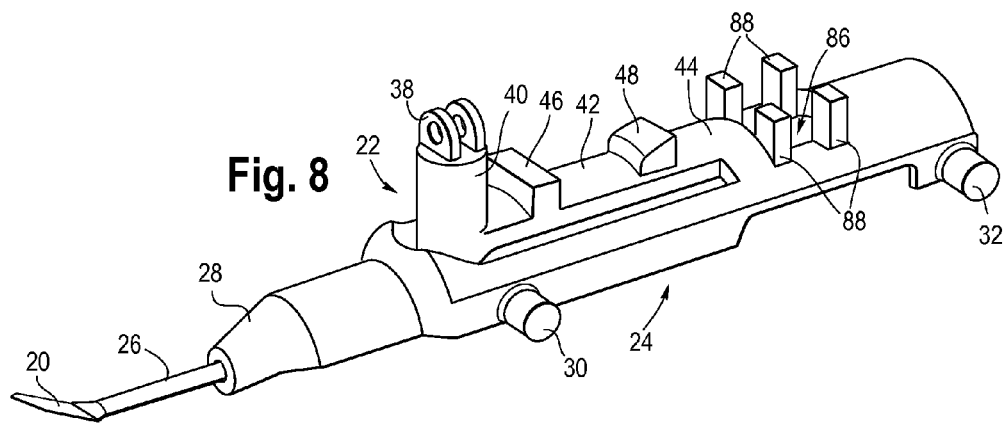
FIG. 8 is a perspective view of the knife carriage.
Figure 12:
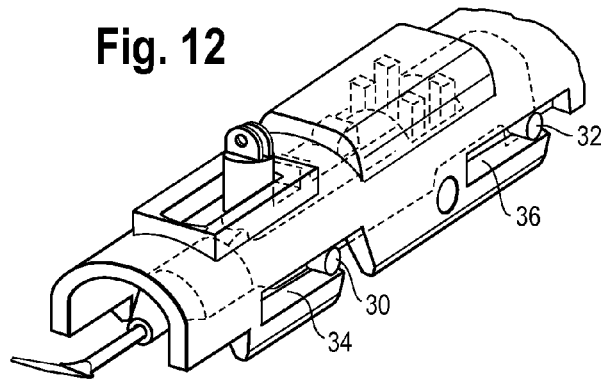
FIG. 12 is a perspective view of the blade carriage.

Referring to FIGS. 4 and 8, actuator 22 is formed as part of a knife carriage 24. Blade 20 is formed as part of blade shaft 26 and is secured to blade carriage 24 at blade mount 28. Front and rear carriage guides 30, 32, formed as opposed pairs on knife carriage 24 and are received in slots 34, 36 formed on the interior of handle 12 as seen in FIG. 12. The combination of guides 30, 32 and slots 34, 36 constrain knife carriage 24 to slide in a straight line longitudinally within handle 12.

As seen in FIG. 8, actuator 22 is formed as an integral part of knife carriage 24 and includes a finger grip 38 extending from an upstanding actuator body portion 40. Body portion 40 is, in turn, integrally attached to a tongue 42 which extends from knife carriage 24 at living hinge 44. As can be appreciated from viewing FIG. 8, when finger grip 38 is pushed downward, tongue 42 flexes to bend about hinge 44. Front and rear stops 46, 48 extend upwardly from tongue 42.

As seen in FIG. 2, a retainer slot 50 is formed in handle 12, rearward of actuator 22. As seen in FIG. 4, when knife carriage 24 is positioned to hold blade 20 in its retracted position, front stop 46 engages retainer slot 50, keeping knife carriage 24 from being moved.

Referring now to FIG. 5, blade 20 is shown in its extended position and it can be seen that carriage 24 has been moved in a forward direction to engage rear stop 48 with retainer slot 50, also keeping knife carriage 24 from being moved.

Referring now to FIGS. 2 and 3, an actuator guide slot 52 is shown formed in the uppermost surface of handle 12. As seen in FIGS. 2 and 3, finger grip 38 of actuator 22 protrudes from and is carried within slot 52. In FIG. 2, finger grip 38 is shown at the rearmost end of slot 52 with knife carriage 24 moved rearward and knife blade 20 shown in its retracted position. In FIG. 3, knife blade 20 is shown in its fully extended position with finger grip of actuator 22 positioned at the forwardmost end of slot 52.

Figure 7:
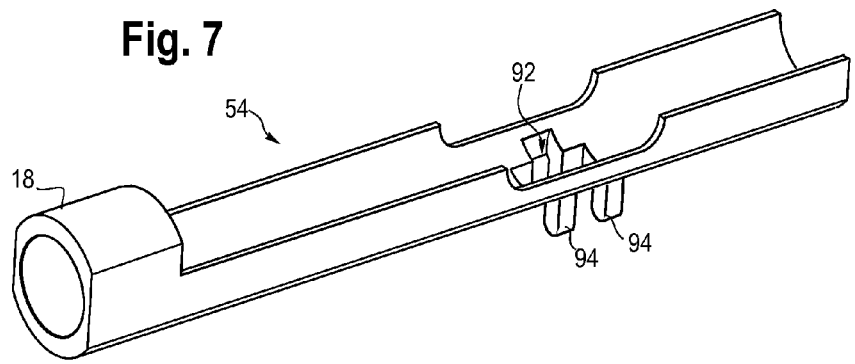
FIG. 7 is a perspective view of the guard carriage.

In order to move knife carriage 24 longitudinally within handle 12, finger grip 38 must be depressed, bending tongue 42 at hinge 44 to disengage stops 46, 48 from slot 50. As an example, in FIG. 4, in order to move knife carriage 24 in a forward direction to extend blade 20, finger grip 38 is depressed or pushed downward to disengage stop 46 from slot 50. Thereafter, finger grip 38 is urged forward along slot 52 until rear stop 48 engages slot 50. In this manner, knife carriage 24 is held in positive engagement with handle 12 when knife 20 is in its fully extended or fully retracted position. Referring now to FIGS. 6 and 7, a guard carriage 54, blade guard 18 is formed as part of guard carriage 54 at the forward end thereof. As seen in FIG. 6, guard carriage 54 is slidably received in the lower half 56 of handle 12. In one embodiment, guard carriage 54 is formed with a pair of opposed flat sides 58, 60 received between and guided by forward guide tabs 62 and rear guide tabs 64. In this manner, guard carriage 54 is slidable longitudinally within handle 12 and is prevented from rotating.

Figure 9:
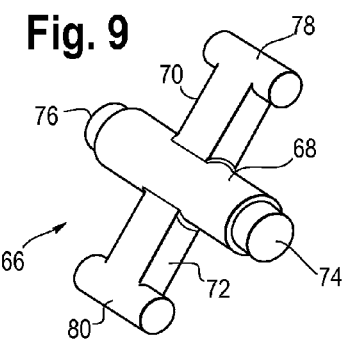
FIG. 9 is a perspective view of the pivot pin.

As seen in FIGS. 6 and 9, a pivot post 66 is positioned within handle 12 and engages guard carriage 54.

As best seen in FIG. 9, pivot post 66 has a central shaft 68 from which upper arm 70 and lower arm 72 extend. At one end of pivot shaft 68, a cylindrical bearing 74 is formed while a similar bearing 76 is formed at the opposite end of pivot shaft 68. Upper arm 70 terminates at a pivot peg 78 while lower arm 72 terminates at a similarly-shaped lower pivot peg 80. In the embodiment shown, upper and lower pivot peg 78, 80 are generally cylindrical in shape and are formed as part of upper and lower arms 70, 72, respectively.

Figure 10:
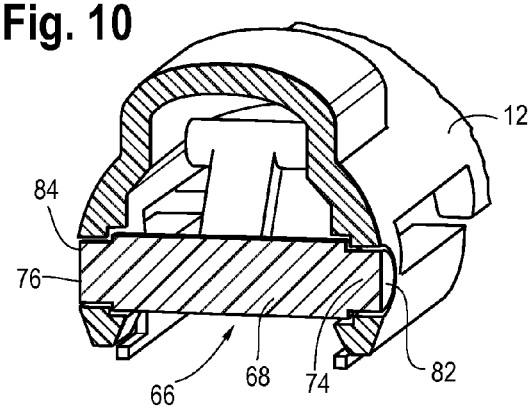
FIG. 10 is a partial sectional perspective view showing the pivot pin mounted to the upper handle.
Figure 11:
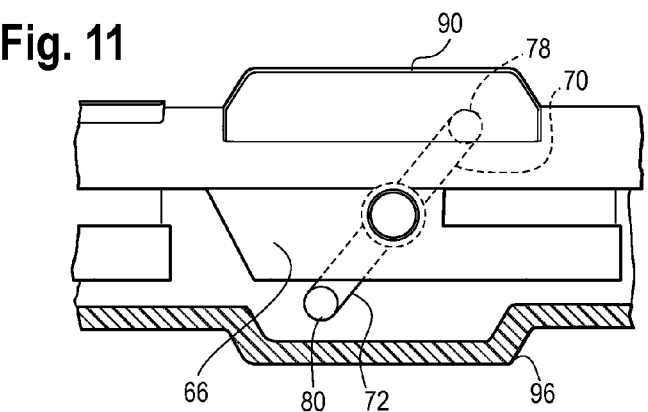
FIG. 11 is a partial lateral view showing the assembly of the upper and lower handles together with the blade carriage pivot pin and guard carriage.

Referring now to FIG. 10, pivot post 66 is seen mounted to handle 12 with pivot bearings 74, 76 rotatably received and, respectively, right socket 82 and left socket 84. In the embodiment shown, bearings 74, 76 are formed as cylindrical projections from pivot shaft 68 and sockets 82, 84 are formed with a corresponding cylindrical shape, whereby pivot shaft 68 is free to rotate within handle 12.

Referring now to FIGS. 4 and 8, pivot post 66 is seen installed within handle 12 with upper peg 78 engaging actuator slots 86 formed on knife carriage 24. A set of guide posts 88 extend upward from slot 86 and are received by handle housing 90 formed as a part of handle 12.

Referring now to FIGS. 4 and 7, a guard carriage actuator slot 92 is formed rearward of guard 18 and is surrounded by a set of posts 94. As seen in FIG. 4, posts 94 are received in lower handle housing 96.

As seen in FIGS. 4 and 5, upper peg 78 of pivot post 66 is sized and shaped to engage knife carriage actuator slot 86 while, at the same time, lower peg 80 of pivot post 66 is sized and shaped and positioned to engage guard carriage actuator slot 92.

The positioning of pivot post 66 with upper and lower arms 70, 72 and upper and lower peg 78, 80 within upper handle housing 90 and lower handle housing 96 is shown with both knife carriage 24 and guard carriage 54 removed. It can be seen that as pivot post 66 is rotated about pivot bearings 74, 76, upper peg 78 and lower peg 80 move within upper and lower housings 90, 96, respectively. It can also be seen from FIG. 4 and FIG. 5 that the movement of pivot post 66 within upper and lower housings 90, 96 is also limited by the engagement and disengagement of front and rear stops 46, 48 with retainer slot 50.

Operation of the features of knife 10 can now be described. As seen in FIG. 4, when blade 20 is in its retracted position, guard 18 is in its extended position. Blade 20 moves, responsive to the movement of blade carriage 24 while guard 18 moves responsive to the movement of guard carriage 54. When, as seen in FIG. 4, finger grip 38 is depressed to disengage forward stop 46 from retainer slot 50 and is then moved forward along slot 52, knife carriage 24 engages upper peg 78 in actuator slot 86 and causes pivot post 66 to rotate about pivot shaft 68.

Lower peg 80 is engaged within guard carriage actuator slot 92 and, as upper peg 78 rotates in the direction of extending blade 20, peg 80 is rotated in the direction of retracting guard carriage 54, thereby moving guard 18 rearwardly into distal end 16 of handle 12.

As seen in FIG. 5, when rear stop 48 is engaged with retainer slot 50, peg 80 has moved guard carriage 54 to its rearmost position. At the same time, knife carriage 24 is at its forwardmost position allowing blade 20 to extend fully outwardly from distal end 16 of handle 12.

In use, when knife 10 is presented with guard 18 fully extended, blade 20 is covered but can be viewed through the transparent material used to form guard 18 so the surgeon can identify the type and orientation of the knife blade. When finger grip 38 is depressed, front stop 46 is disengaged from slot 50 and knife carriage 24 is moved forward until rear stop 48 engages retainer slot 50. In this position, guard 18 is retracted and knife 20 has been moved forward responsive to the motion of knife carriage 24 to place blade 20 in an operative position for surgery. When the knife is no longer needed, the surgeon pushes down on finger grip 38 to disengage rear stop 48 from slot 50 and moves finger grip 38 along slot 52 until front stop 46 engages slot 50.

Figure 13:
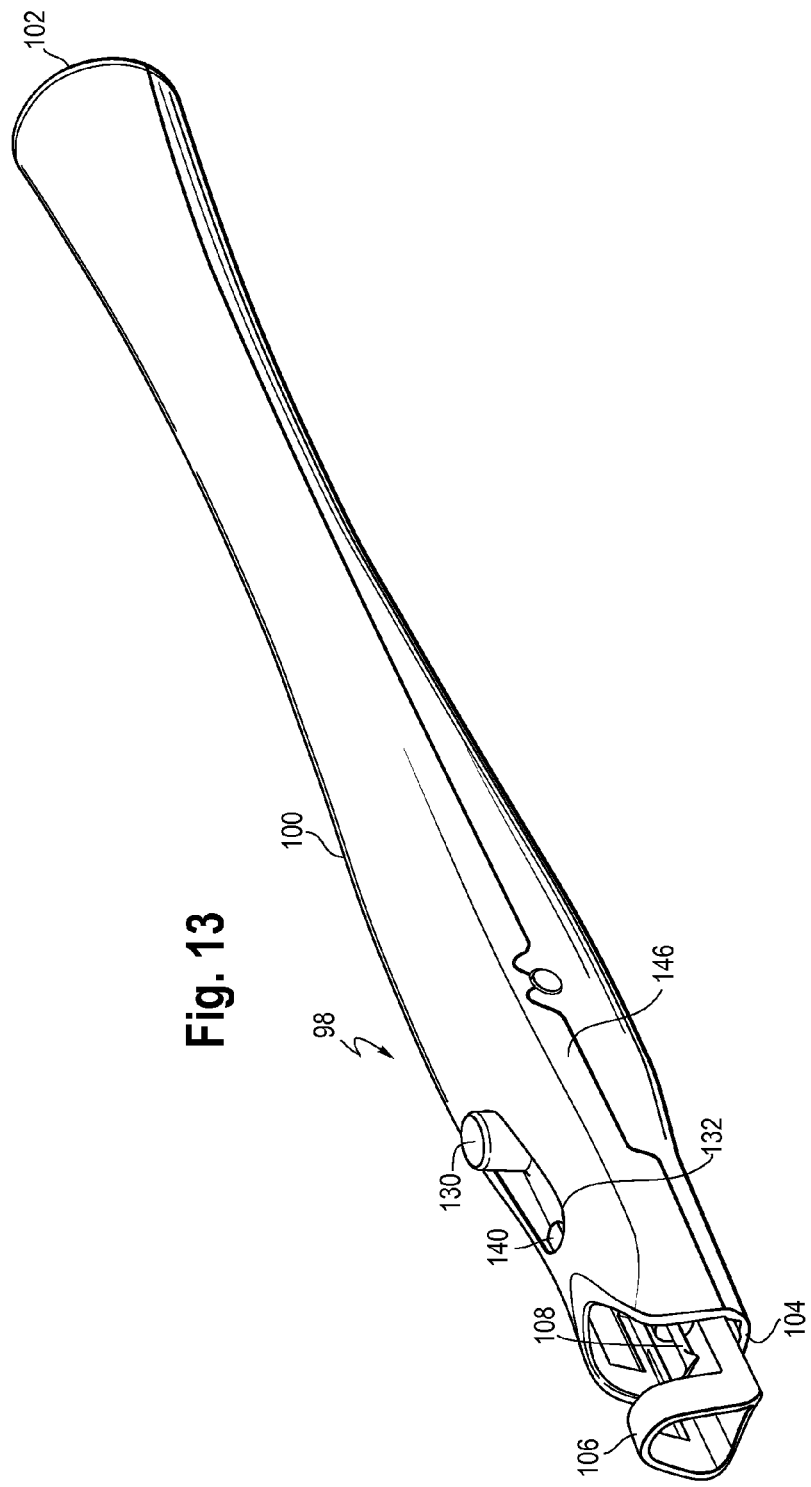
FIG. 13 is a perspective view of another embodiment of the invention with the blade guard retracted and the blade extended.

Referring now to FIG. 13 the numeral 98 identifies a knife comprising an additional embodiment of the present invention.

Knife 98 has a handle 100, which has a proximal end 102 and a distal end 104. A blade guard 106 extends from distal end 104 of handle 100 and is preferably sized and shaped to surround and protect a surgical blade 108 which also extends from distal end 104.

Referring now to FIG. 14, it can be seen that guard 106 is formed as an integral portion of guard carriage 110. In the embodiment shown, guard 106 is formed as an arch 112 having a pair of depending legs 114, 116 joined to carriage 110. As described hereinabove, guard 106 can be formed from a transparent material to allow blade 108 to be seen when guard 106 is extended to cover blade 108.

Referring now to FIG. 15 the numeral 118 identifies a combined blade carriage and actuator having a blade mount 120 fashioned at one end thereof adapted to receive and hold blade 108. Carriage 118 has a body 122 on which is formed an actuator tongue 124 which is partially severed from body 122 along a tongue slot 126. The material from which carriage 118 is fashioned allows tongue 124 to flex with respect to body 122 at a living hinge 128. An actuator button 130 is formed on tongue 124 to effect such flexing action when desired. A locking tab 132 is formed at end 134 of tongue 124, it being understood that end 134 is free to move responsive to the motion of actuator button 130.

Figure 16:
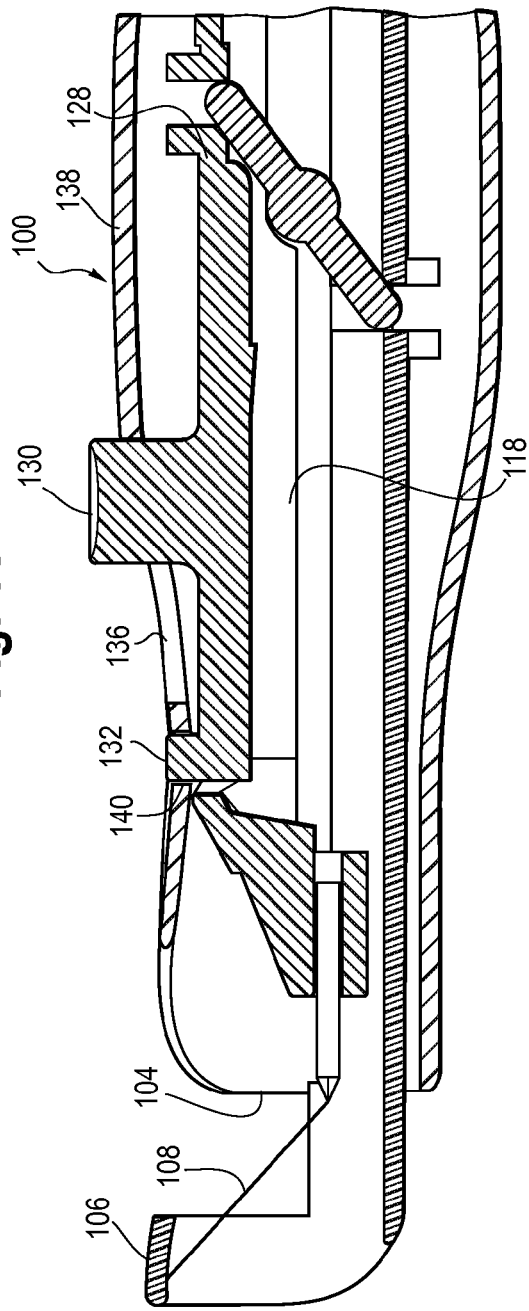
FIG. 16 is a partial sectional view of the device shown in FIG. 13.

Referring now to FIG. 16, a portion of handle 100 is shown within which carriage 118 is slidably received. It should be understood that the mechanism by which carriage 118 and guard 106 are retracted and extended is substantially as described earlier with respect to FIGS. 4-12.

As seen in FIG. 16, a longitudinally-extending actuator slot 136 is formed through wall 138 of handle 100, through which actuator button 130 extends when carriage 118 is inserted into handle 100. A locking slot 140 is formed through wall 138 intermediate slot 136 and handle end 104. When in the guarded position, with guard 106 covering blade 108, locking tab 132 is engaged in locking slot 140, preventing movement of carriage 118. Engagement of locking tab 132 in slot 140 is also shown in FIG. 13.

In order to move guard 106 and blade 108 to the open, or unguarded position, locking tab 132 must be disengaged from slot 140 to allow actuator button 130 to be moved along slot 136. This is accomplished by pushing down on actuator button 130 until tongue 124 is bent downward sufficiently to move tab 132 clear of slot 140. Actuator button 130 can then be moved longitudinally along slot 136 toward handle end 104, responsive to which guard 106 is retracted as blade 108 is extended.

Figure 17:
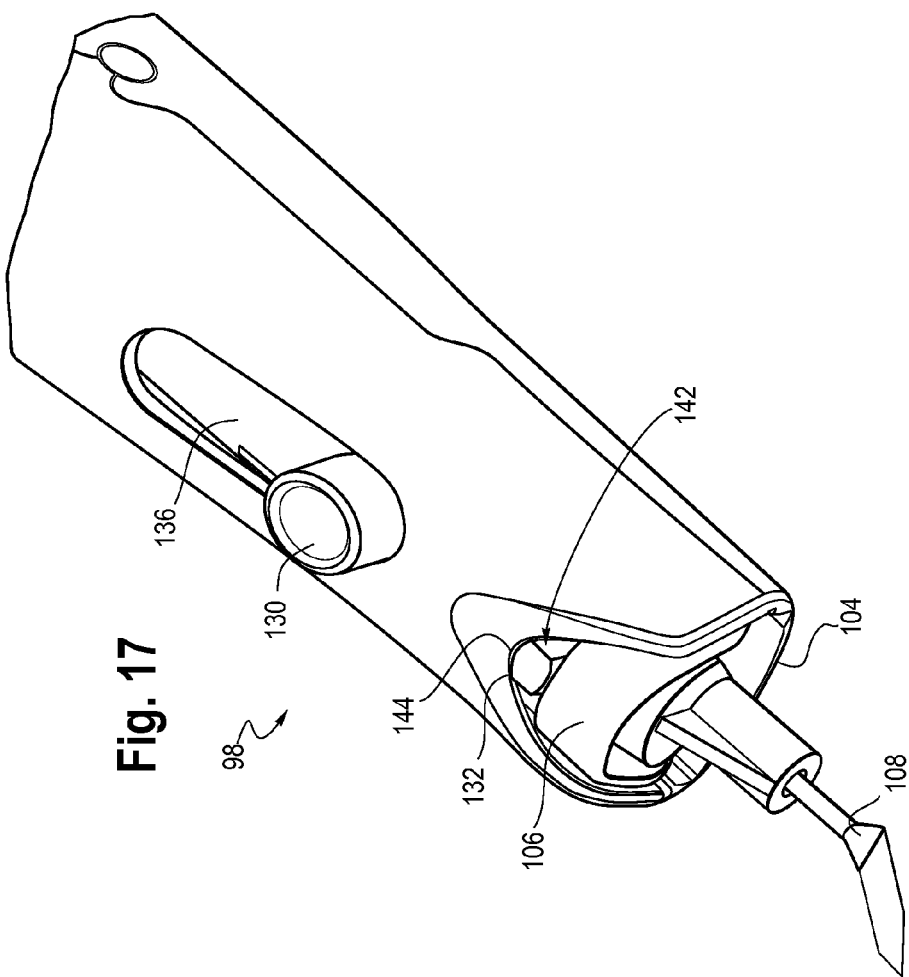
FIG. 17 is a partial perspective view of the device of FIG. 13 with the blade extended and the guard retracted.

Referring now to FIG. 17 an enlarged, partial perspective view of knife 98 is shown with guard 106 fully retracted and blade 108 fully extended. As seen, actuator button 130 is positioned within that portion of slot 136 closest to handle end 104.

As further seen in FIG. 17, a mouth 142 is defined by handle end 104, and mouth 142 includes a bight 144 extending generally in an arc about the upper surface of handle 100 (FIG. 16). It is a feature of this embodiment that when actuator button 130 is moved forward in slot 136, carriage 118 (FIG. 18) is responsively moved forward a sufficient distance to allow locking tab 132 to extend upward to engage bight 144. This action locks carriage 118 (FIG. 18) and, thereby, blade 108 in an exposed position for use in surgery.

Figure 18:
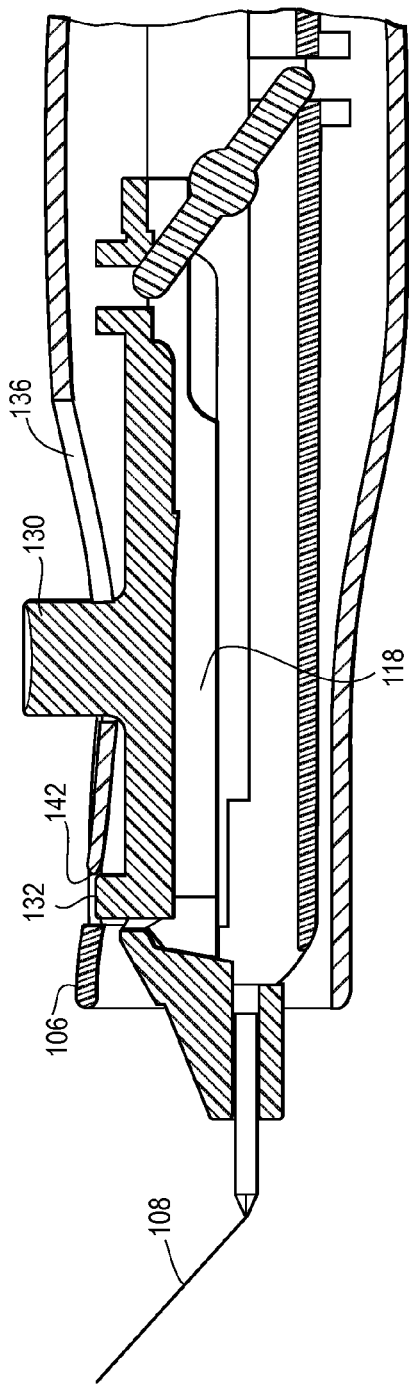
FIG. 18 is a partial sectional view of the device shown in FIG. 17.

Referring to FIG. 18, blade 108 is shown in its locked and extended position, with actuator button 130 moved forward in slot 136 sufficiently to move carriage 118 to allow locking tab 132 to engage bight 144. To retract blade 108 and extend guard 106, actuator button 130 is depressed a sufficient distance to disengage locking tab 132 from bight 144, allowing carriage 118 to slide rearward responsive to the rearward motion of actuator button 142. It is anticipated that the positioning of actuator button 130 on handle 100 (FIG. 16) will allow most users to extend and retract blade 108 without having to reposition the user's hand on knife 98 (FIG. 13).

Figure 19:
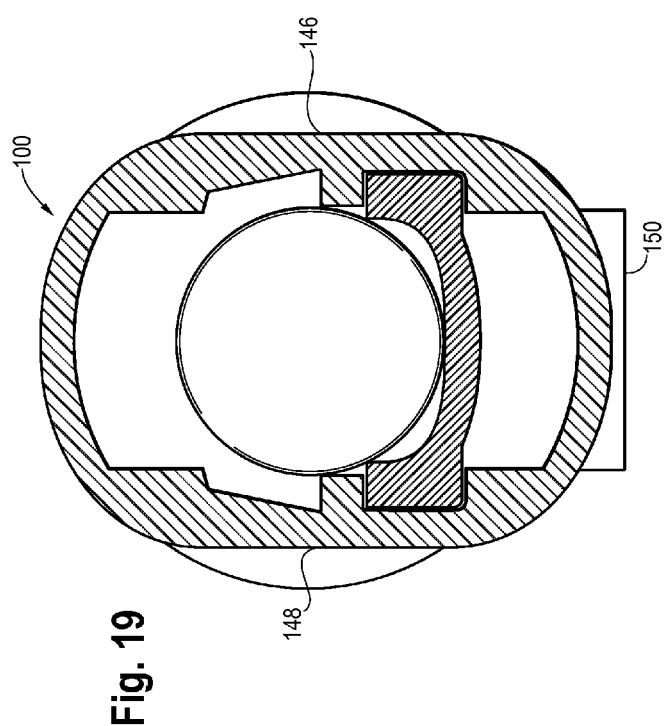
FIG. 19 is a sectional view of the device shown in FIG. 13.

Referring again to FIG. 13, handle 100 is shown having a flattened surface portion 146 positioned where a user would grip handle 100. As seen in FIG. 19, a cross-section of handle 100 shows a corresponding flattened surface portion 148 positioned opposite portion 146. Flattened portions 146, 148 form a grip and a guide to the orientation of blade 108. When a user's hand engages flats 146, 148 with actuator button 130 facing upward, knife 98 is then held in a position to place blade 108 in its operative position. Each time a user grips flats 146, 148 as described, the user knows that blade 108 is facing in its operative position.

FIG. 19 also depicts the placement of a handle prop 150 at the proximal end of handle 100 to act as a support and to keep handle 100 from rolling over from its upright position.

Figure 20:
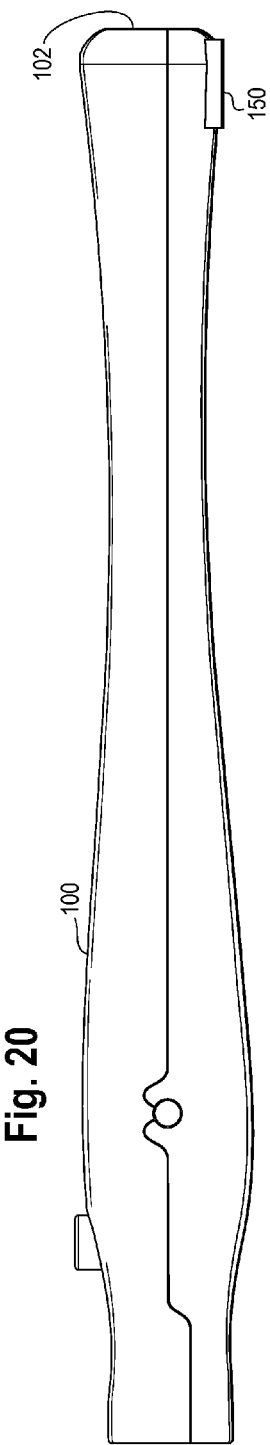
FIG. 20 is a lateral elevational view showing a handle prop.

FIG. 20 shows a preferred placement of prop 150 in relation to the proximal end 102 of handle 100. Prop 150 may be permanently deployed or may be adapted to be removed from or inserted into handle 100 when not in use.

Thus, when blades 20, 108 are in their fully extended position, they are locked in place and cannot be inadvertently moved rearward. In similar fashion, when blade 20 is moved rearward to re-engage front stop 46 with retainer slot 50, guard 18 is locked in place in its fully extended position and blade 20 has been retracted sufficiently to position it wholly within guard 18, and when blade 108 is moved rearward, locking tab 132 re-engages locking slot 140 to do the same.

Because they are locked in place, guards 18, 106 cannot be easily accidently moved rearward to expose blades 20, 108.

In this manner, knives 10, 98 may be used several times during a single surgery with their respective guards being extended and blades being retracted between uses to protect against damage to the blade and accidental cuts.

What is claimed is:

1. A surgical knife, said knife comprising:
   a hollow handle having a proximal end and an operative, distal end, said handle having a handle wall defining an interior handle cavity;
   a blade holder slidably received within said handle cavity at said distal end;
   a blade mounted to said blade holder configured to move between (i) an operating position, wherein said blade extends away from said distal end, and (ii) a guarded position, wherein said blade is retracted toward said distal end;
   a blade guard slidably received within said handle cavity proximate said distal end, said blade guard movable responsive to movement of said blade holder,
   a latch for latching said blade and said guard in both of said operating and guarded positions; and
   a link pivotally mounted within said handle cavity, a first end of said link pivotally engaging said blade guard, a second end of said link pivotally engaging said blade holder whereby when said blade holder is moved in a first longitudinal direction said blade guard is moved in a second, opposite longitudinal direction such that said blade guard is configured to at least partially retract into said handle distal end when said blade holder is moved in a distal direction, and said blade guard is configured to extend from said handle distal end when said blade holder is moved in a proximal direction.

2. The surgical knife as recited in claim 1 wherein said latch comprises (i) a latching slot formed in said handle wall, (ii) first and second latching tabs, said first latching tab being sized and positioned to engage said latching slot when said blade and said blade guard are in said operating position, and said second latching tab being sized and positioned to engage said latching slot when said blade and said blade guard are in said guarded position.

3. The surgical knife as recited in claim 1 wherein said handle further comprises a handle mouth formed at said distal end, said handle mouth having a bight formed thereat in said handle wall; and wherein said latch has (i) a latching tab, and (ii) a latching slot formed in said handle wall, said bight being sized and positioned to positively engage said latching tab when said blade and said guard are in said operating position, and said latching slot being sized and positioned to engage said latching tab when said blade and said guard are in said guarded position.

4. The surgical knife as recited in claim 1 wherein said handle further comprises at least one flat surface formed thereon to indicate the position of said blade when said knife is held by a user.

5. The surgical knife as recited in claim 4 wherein said at least one flat surface comprises a pair of opposed, flat surfaces formed on said handle, said surfaces positioned to orient said blade in an operative position with respect to the hand of said user when said surfaces are gripped by said hand.

6. The surgical knife as recited in claim 1 wherein said handle further comprises a longitudinally-extending guide slot formed in said handle wall, an actuator being formed on said blade holder and sized and positioned to extend through said guide slot, said guide slot thereby constraining the movement of said actuator to a linear motion along a fixed distance.

7. The surgical knife as recited in claim 1 wherein said handle further comprises a longitudinally-extending guide slot formed in said handle wall, and an actuator being formed on said blade holder and sized and positioned to extend through said guide slot, said guide slot thereby constraining the movement of said actuator to a linear motion along a fixed distance, and when said blade holder is moved in said first longitudinal direction said blade guard is moved in said second, opposite longitudinal direction responsive to the movement of said actuator in said guide slot.

8. The surgical knife as recited in claim 1 wherein said handle further comprises a handle prop mounted to said handle.

* * * * *